(12) United States Patent
He

(10) Patent No.: US 9,326,506 B2
(45) Date of Patent: May 3, 2016

(54) PREPARATION METHOD, AGRICULTURAL COMPOSITION AND APPLICATIONS OF NATURAL BRASSINOLIDE ANALOGS

(75) Inventor: Qiming He, Chengdu (CN)

(73) Assignee: CHENGDU NEWSUN CROPSCIENCE CO., LTD, Chengdu (CN)

( * ) Notice: Subject to any disclaimer, the term of this patent is extended or adjusted under 35 U.S.C. 154(b) by 0 days.

(21) Appl. No.: 14/371,216

(22) PCT Filed: Aug. 28, 2012

(86) PCT No.: PCT/CN2012/001156
§ 371 (c)(1),
(2), (4) Date: Jul. 9, 2014

(87) PCT Pub. No.: WO2013/106975
PCT Pub. Date: Jul. 25, 2013

(65) Prior Publication Data
US 2015/0005169 A1    Jan. 1, 2015

(30) Foreign Application Priority Data
Jan. 18, 2012 (CN) .......................... 2012 1 0026285

(51) Int. Cl.
| | | |
|---|---|---|
| *A01N 43/02* | (2006.01) |
| *A01N 35/00* | (2006.01) |
| *A01N 35/04* | (2006.01) |
| *A01N 43/22* | (2006.01) |
| *A01N 45/00* | (2006.01) |
| *C07J 9/00* | (2006.01) |
| *A01N 65/00* | (2009.01) |
| *A01N 65/08* | (2009.01) |
| *C07J 73/00* | (2006.01) |

(52) U.S. Cl.
CPC ................. *A01N 35/04* (2013.01); *A01N 43/22* (2013.01); *A01N 45/00* (2013.01); *A01N 65/00* (2013.01); *A01N 65/08* (2013.01); *C07J 9/00* (2013.01); *C07J 73/003* (2013.01)

(58) Field of Classification Search
CPC .......................................................... C07J 9/00
USPC .................................................. 504/140, 348
See application file for complete search history.

(56) References Cited

FOREIGN PATENT DOCUMENTS

| CN | 1217337 A | 5/1999 |
| CN | 1217338 A | 5/1999 |
| RU | 2 434 877 C1 | 11/2011 |

OTHER PUBLICATIONS

Zullo et al. Braz.J.Plant.Physiol. 2002, 14(3), 143-181.*
International Search Report (PCT/ISA/210) mailed on Dec. 6, 2012, by the Chinese Patent Office as the International Searching Authority for International Application No. PCT/CN2012/001156.
Michael D. Grove et al., "Brassinolide, A Plant Growth-Promoting Steroid Isolated From Brassica Napus Pollen", Nature, vol. 281, No. 5728, Sep. 20, 1979, pp. 216-217.
Marco Antonio Teixeira Zullo et al., "Brassinosteroid Phytohormones—Structure, Bioactivity and Applications", Brazilian Journal of Plant Physiology, Dec. 31, 2002, vol. 14, No. 3, pp. 143-181.
Wei-Ming Zhu et al., "The Selective Dehydroxylation of 20-Hydroxyecdysone by Zn Powder and Anhydrous Acetic Acid", Synthetic Communications, vol. 32, No. 9, 2002, pp. 1385-1391.
Apichart Suksamrarn et al., "Stereoselective Catalytic Hydrogenation of $\Delta^7$-6-Ketosteroids in the Presence of Sodium Nitrite", Tetrahedron, vol. 58, 2002, pp. 6033-6037.

* cited by examiner

*Primary Examiner* — Nizal Chandrakumar
(74) *Attorney, Agent, or Firm* — Buchanan Ingersoll & Rooney PC

(57) ABSTRACT

The present invention provides extraction methods and uses of brassinolide analogs extracted from a plant, including the uses for the promotion of growth, resistance to low temperature and salt tolerance of a plant. Furthermore, the present invention also provides agricultural compositions comprising the brassinolide analogs.

13 Claims, 4 Drawing Sheets

A

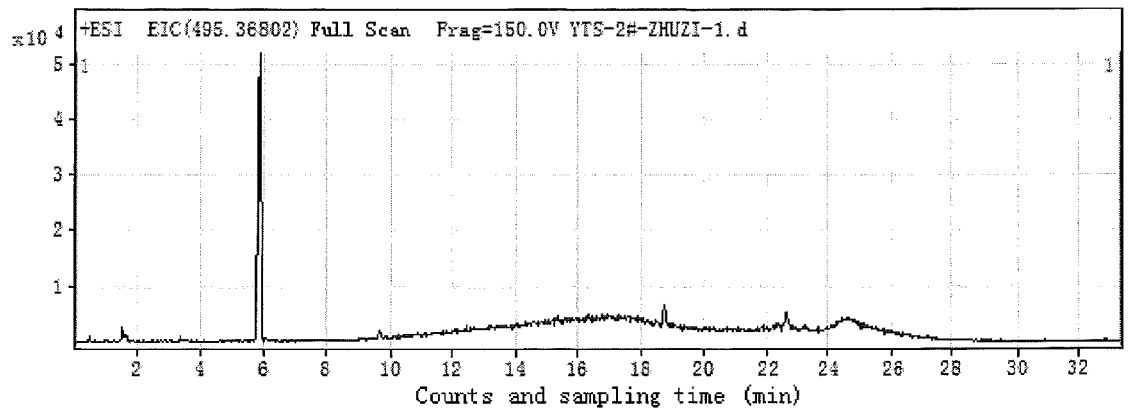
B
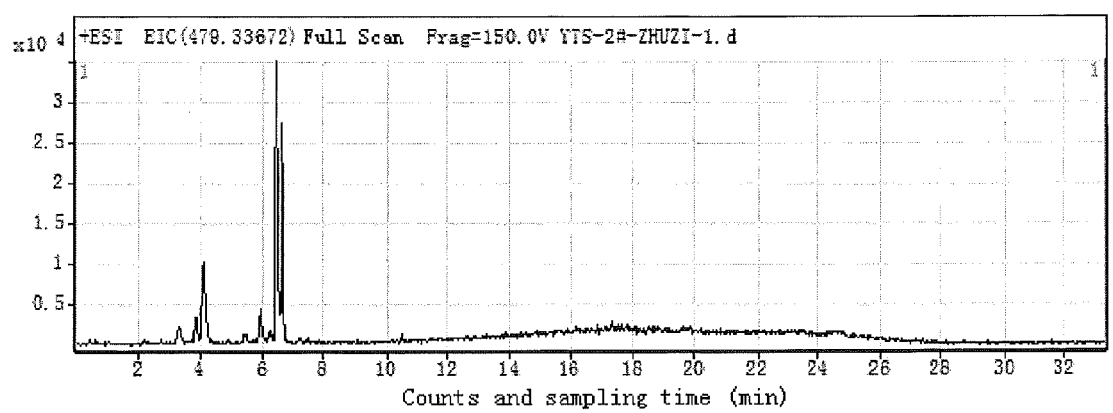
C
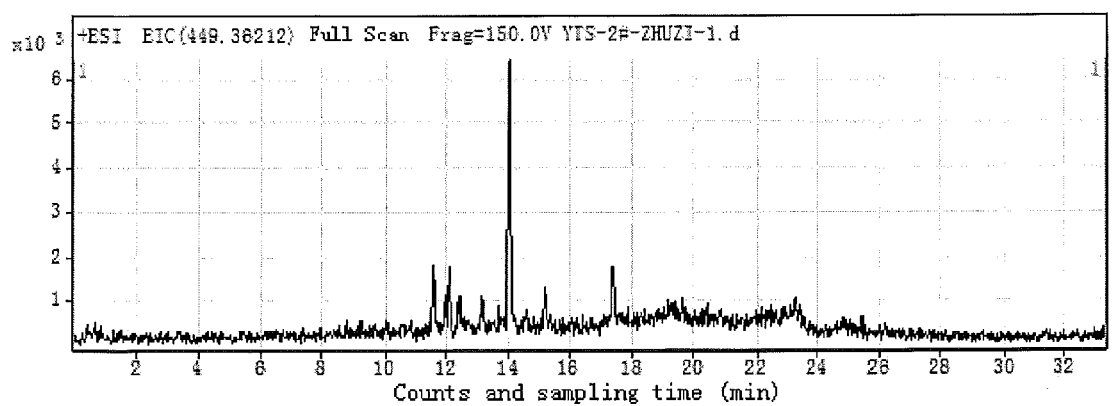
D
Figure 2 (continue)

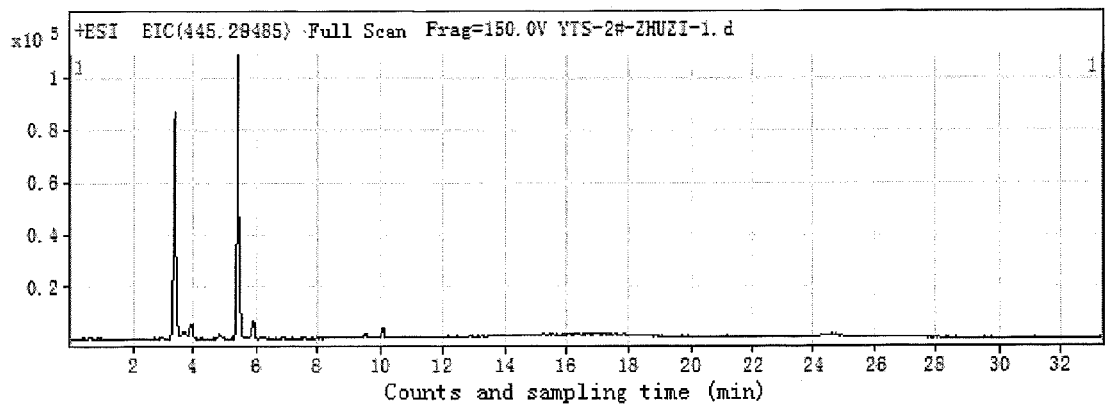
E
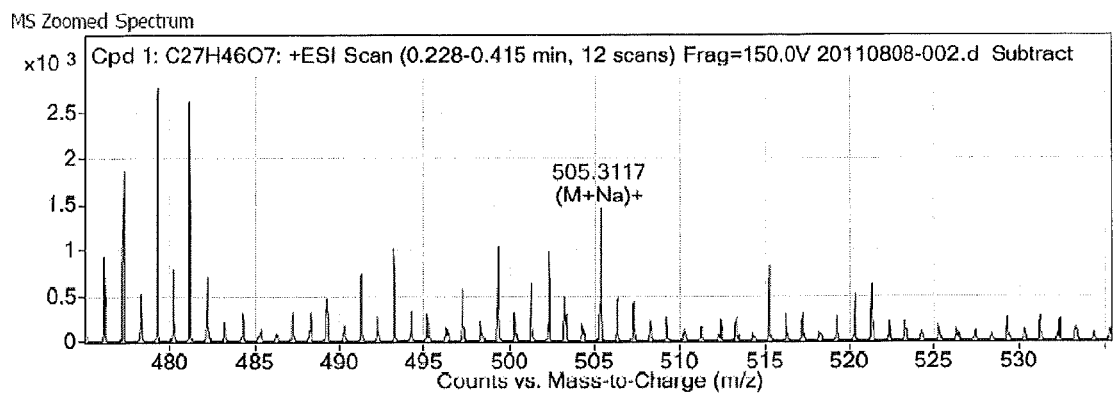
F
Figure 2 (continue)

PREPARATION METHOD, AGRICULTURAL COMPOSITION AND APPLICATIONS OF NATURAL BRASSINOLIDE ANALOGS

FIELD OF THE INVENTION

The present invention belongs to the field of agricultural chemical technology. Specifically the present invention relates to brassinolide analogues extracted from a plant and uses thereof, including the uses for the promotion of growth, resistance to low temperature and salt tolerance of a plant.

BACKGROUND OF THE INVENTION

Brassinolide is internationally recognized as an efficient, broad-spectrum and non-toxic plant growth regulator. Its effect is higher than the other five types of plant hormones, so the most active regulator is known as sixth type of plant hormone in the world. Brassinolide is widely found in angiosperms, gymnosperms, and some lower plants. From the perspective of the distribution in a plant, it exists in the roots, stems, leaves, pollens, pistils, fruits and seeds. For example, pollens of canola contain relatively abundant brassinolide.

Although chemically synthesized brassinolide or analogues thereof, as mentioned in Chinese patent applications CN1217337A, CN1217338A and so on, are pure, yet their long-term effects are usually not as good as those of naturally-extracted brassinolide products due to its single component. The phenomenon was particularly prominent on 28-homo-brassinolide which had been widely used in China.

A brassinolide product extracted from a plant (e.g., pollens) or other natural sources (e.g., beeswax) usually contains several types of structural analogues of brassinolide. It's much easier for domestic and foreign users to promote the use of the natural product. However due to its preparation, its quality is difficult to be stable. If it is further purified, the product is not conducive to industrialization due to increased costs, so that people is impeded to further purify a large amount of the product and to research the activities of brassinolide analogues isolated from it. For example, Zhu, W. M., et al (Synthetic Communications, 32(9), 1385-1391) and Suksamararn, A., et al (Tetrahedron, 58, 6033-6037) synthesized a series of compounds, but the compounds are recognized as ecdysteroid analogues from an insect for the use of ecdysteroid.

Through long-term and arduous efforts, the inventor explored a stable process of extracting (purified) brassinolide analogues from a plant. The inventor carefully studied the various extraction solvents in the process. Although the process needs certain extraction steps, yet various isolated purified natural brassinolide analogues can be collected at one time and shares costs of extraction, so that the process is conducive to industrialization. In addition, the isolated natural brassinolide analogues can be applied alone, or be mixed at a certain ratio and then applied, so that the quality of the applied product is stable and easily controlled. On the basis of a large amount of isolated purified natural brassinolide analogues, the inventor surprisingly found that the natural brassinolide analogues had effects on the promotion of growth, resistance to low temperature and salt tolerance of a plant, and under certain conditions, their effects and activities were higher than those of chemically synthesized brassinolide products in prior arts.

DISCLOSURE OF THE INVENTION

The problem to be solved by the present invention is to provide novel extraction methods and uses of natural brassinolide analogues, including the uses for the promotion of growth, resistance to low temperature and/or salt tolerance of a plant. Furthermore, the present invention also provides component proportion-stable agricultural compositions comprising the natural brassinolide analogues.

Specifically in first aspect, the invention provides an extraction method of natural brassinolide analogues, which comprises the steps of (1) extracting crushed canola pollens by using 80~100% (V/V) aqueous ethanol solution, and retaining filtrate after solid-liquid separation (optionally further concentrating the filtrate), for obtaining an alcohol-soluble liquid extract;

(2) mixing the alcohol-soluble liquid extract and 0~60% (V/V) aqueous ethanol solution, then adding ethyl acetate for extraction, retaining ethyl acetate layer, adding esterase and glucoamylase to the layer for an incomplete reaction, and then drying the layer, for obtaining an ester-soluble extract;

(3) loading the ester-soluble extract on a silica gel chromatographic column, eluting by using a mixture of methanol and ethyl acetate, collecting eluent comprising natural brassinolide analogues, drying and dissolving the eluent into methanol, for obtaining a silica gel column-purified liquid; and (4) loading the silica gel column-purified liquid on a C18 reversed-phase chromatographic column, eluting by using a mixture of acetonitrile and water, respectively collecting eluent comprising natural brassinolide analogues of formulae BR6, BR1, BR2, BR3, BR4 and/or BR5.

The word "natural" used herein means the substance defined by the word is extracted from a natural source (e.g., pollens, beeswax and so on). In an embodiment of the invention, the brassinolide analogues are extracted from canola pollens. Because they are analyzed, the natural brassinolide analogues are not limited to be extracted from a natural source (e.g., pollens, beeswax and so on), and they can be chemically synthesized.

The natural brassinolide analogues of formulae BR6, BR1, BR2, BR3, BR4 and/or BR5, used herein, are shown below:

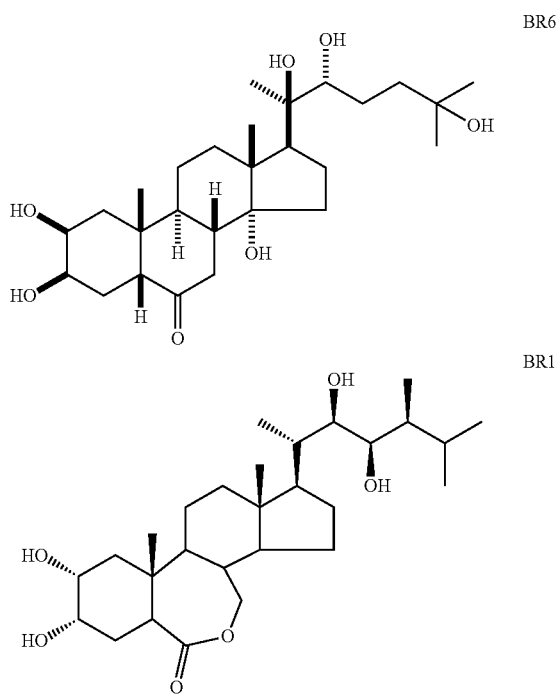

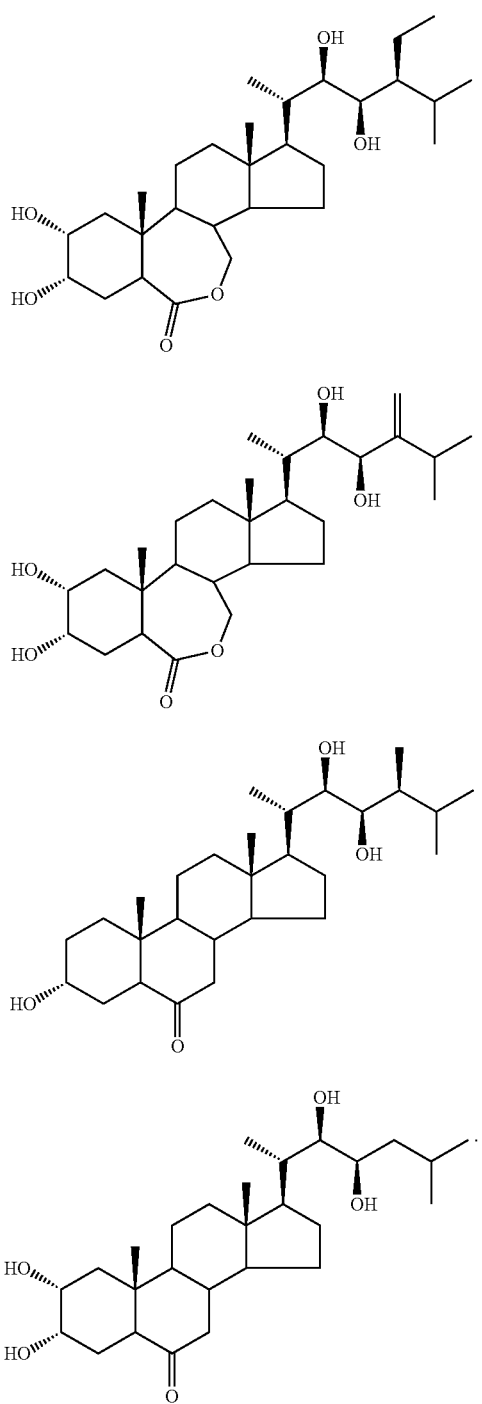

The natural brassinolide analogues mentioned above can be produced by successive elution of the extraction method mentioned in the embodiment of the invention, and their identification spectra are respectively shown in FIG. 2A~FIG. 2F. In an embodiment of the invention, BR1, BR5 and/or BR6 is more preferable, especially BR6 is the most preferable.

In step (1) of the method of first aspect of the invention, 100% (V/V) aqueous ethanol solution (i.e., pure ethanol) can be used. However, preferably the concentration of the aqueous ethanol solution is 85~98% (V/V), preferably 90~97% (V/V), more preferably 93~96% (V/V), most preferably 95% (V/V).

In step (1) of the method of first aspect of the invention, generally a method of crushing canola pollens is a physically crushing method, including ultrasonic disruption, milling and so on.

In step (1) of the method of first aspect of the invention, the weight-to-volume ratio of the canola pollens:the aqueous ethanol solution can be optimized. Lower ratio would result in more ethanol and more cost, while higher ratio would result in incomplete extraction. According to the inventor's research, preferably in step (1), the weight-to-volume ratio of the canola pollens:the aqueous ethanol solution is 50~200 g:200~500 mL, preferably 80~150 g:250~450 mL, more preferably 90~120 g:280~350 mL, most preferably 100 g:300 mL.

After the extraction of step (1), the filter residue can be further extracted for a complete extraction, and the extraction step of the filter residue can be repeated. All of the filtrate obtained after each extraction are combined. Therefore, preferably the step (1) of the method of first aspect of the invention further comprises the steps of extracting filter residue obtained from the solid-liquid separation by using 80~100% (V/V) aqueous ethanol solution, carrying out solid-liquid separation, and retain filtrate for the combination with the filtrate obtained from step (1). The conditions of the additional step may be the same as those of other extraction step of step (1). The filter residue obtained from the solid-liquid separation can be further extracted 0~5 times under the same conditions, and all of filtrate are combined.

In step (1), more volume of the filtrate or the combined filtrate is not conducive to the efficiency of extraction. Therefore, preferably in step (1) of the method of first aspect of the invention, the filtrate is further concentrated. Concentrating is concentrating by drying under reduced pressure, preferably drying at 65~80° C. and vacuum degree of 0.08~0.09 Mpa, most preferably drying at 75° C. and vacuum degree of 0.085 Mpa. After the concentration, preferably the volume ratio of the alcohol-soluble liquid extract:the aqueous ethanol solution used in step (2) is 0.5~2:1~3, preferably 0.8~1.5:1.5~2.5, most preferably 1:2.

In step (2) of the method of first aspect of the invention, although 0% (V/V) aqueous ethanol solution (i.e., pure water) can be used, yet preferably the concentration of the aqueous ethanol solution is 30~55% (V/V), preferably 40~53% (V/V), more preferably 45~52% (V/V), most preferably 50% (V/V).

In step (2) of the method of first aspect of the invention, the amount of ethyl acetate for addition can be optimized. According to the inventor's research, preferably in step (2), the volume ratio of the aqueous ethanol solution:the ethyl acetate is 1~3:3~8, preferably 1.5~2.5:4~6, most preferably 2:5.

After the extraction of step (2), non-ethyl acetate layer (i.e., the remaining layer after separating off the ethyl acetate layer) can be further extracted for a complete extraction, and the extraction step of the non-ethyl acetate layer can be repeated. All of the non-ethyl acetate layers obtained after each extraction are combined. Therefore, preferably step (2) of the method of first aspect of the invention further comprises the steps of adding ethyl acetate to non-ethyl acetate layer for extraction, and retaining ethyl acetate layer for the combination with the ethyl acetate layer obtained from step (2). The extraction can be carried out 1~8 times, preferably 2~5 times.

Preferably in step (2) of the method of first aspect of the invention, an esterase, also named as a lipase, is capable of hydrolyzing triglycerides or fatty acid esters to produce mono- or di-glycerides and free fatty acids. The enzyme is widely used in the food industry. Preferably the esterase is an esterase extracted from a bacterium. For example, it is a commercially available esterase or an esterase extracted directly from a bacterium (e.g., Pseudomonas fluorescens, preferably a strain of CGMCC No. 1.867 (i.e., AS 1.867)) (see Chinese patent application No. 200810046182.0).

Preferably in step (2) of the method of first aspect of the invention, a glucoamylase, also named as a saccharifying enzyme, is capable of converting starch chains into glucose. The enzyme is widely used in the brewing industry. Preferably the glucoamylase is a glucoamylase extracted from a fungus. For example, it is a commercially available glucoamylase or a glucoamylase extracted directly from a fungus (e.g., *Aspergillus niger*).

The words "incomplete reaction" used herein mean terminating the reaction before an enzyme converts all of the substrate. The incomplete reaction results in diversity of natural brassinolide analogues. Generally more than 3 hours is needed for a complete reaction, so preferably in step (2) of the method of first aspect of the invention, the incomplete reaction is a reaction at 35~42° C. for 0.5~2 hr, preferably at 37~41° C. for 0.75~1.5 hr, most preferably at 40° C. for 1 hr.

Preferably in step (2) of the method of first aspect of the invention, drying is drying under reduced pressure, preferably drying at 65~80° C. and vacuum degree of 0.08~0.09 Mpa, most preferably drying at 75° C. and vacuum degree of 0.085 Mpa.

The inventor found that a silica gel chromatographic column was suitable for the initial purification, and various natural brassinolide analogues can be easily and sufficiently collected by just setting the start and ending point according to elution rate. Preferably in step (3) of the method of first aspect of the invention, the packing of the silica gel chromatographic column is 200~300 mesh silica gel, most preferably 300 mesh silica gel.

Elution agents potentially used in step (3) are various. According to the inventor's research, elution by using a mixture of methanol and ethyl acetate can result in more stable products. Preferably in step (3) of the method of first aspect of the invention, the volume ratio of methanol:ethyl acetate of the mixture is 3~8:0.5~1.5, preferably 4~7:0.8~1.3, most preferably 5:1.

Preferably in step (3) of the method of first aspect of the invention, drying is drying under reduced pressure, preferably drying at 65~80° C. and vacuum degree of 0.08~0.09 Mpa, most preferably drying at 75° C. and vacuum degree of 0.085 Mpa.

Elution agents potentially used in step (4) are various. According to the inventor's research, elution by using a mixture of acetonitrile and water can result in efficient separation of various natural brassinolide analogues. Preferably in step (4) of the method of first aspect of the invention, the volume ratio of acetonitrile:water of the mixture is 60~90:10~40, preferably 70~80:20~30, most preferably 75:25.

The purity of the natural brassinolide analogues obtained from the extraction method of first aspect of the invention is high. Preferably in step (4) of the method of first aspect of the invention, the purity of natural brassinolide analogues of formulae BR6, BR1, BR2, BR3, BR4 and/or BR5 is more than 90%, preferably more than 95%, more preferably more than 98%, most preferably more than 99%.

In second aspect, the invention provides an agricultural composition, which is obtained by mixing isolated natural brassinolide analogues of formulae BR6, BR1, BR2, BR3, BR4 and/or BR5 and an agriculturally acceptable auxiliary material.

The words "agriculturally acceptable auxiliary material" used herein mean an agricultural material which does not interfere with or even does enhance effects of the natural brassinolide analogues, including excipient, diluent, emulsifying agent, pH adjusting agent and so on. In an embodiment of the invention, the agriculturally acceptable auxiliary material is water.

Preferably in the agricultural composition of second aspect of the invention, the natural brassinolide analogues are extracted by the extraction method of first aspect of the invention, and more preferably, the purity of the natural brassinolide analogues is more than 90%, preferably more than 95%, more preferably more than 98%, most preferably more than 99%.

The word "isolated" used herein means that the natural brassinolide analogues are or were out of its naturally occurring environment, and they do or did exist with their purity of more than 50%. Although the natural brassinolide analogues can be mixed into a mixture so that their purity can be decreased, yet the previous state of high purity can result in the good stability among batches of the product. Preferably the agricultural composition of second aspect of the invention is a component proportion-stable agricultural composition. The words "component proportion-stable" used herein mean the same compositions and contents of natural brassinolide analogues among different batches of the product. Since they are separated by the method of first aspect of the invention, the natural brassinolide analogues can be used alone or formulated in a certain proportion. So they can be component proportion-stably used. In an embodiment of the invention, the contents of the natural brassinolide analogues is in the range of 0.0005~0.05 ppm, e.g., 0.005 ppm. Natural brassinolide analogues of formulae BR6, BR1, BR2, BR3, BR4 and/or BR5 can be used alone or mixed. When they are mixed, the weight ratio of BR1:BR2:BR3:BR4:BR5:BR6 may be 0.01~100:0.01~100:0.01~100:0.01~100:0.01~100:0.01~100. In an embodiment of the invention, the weight ratio of BR1:BR2:BR3:BR4:BR5:BR6 is 0.4:0.4:0.4:0.4:0.4:98.

In third aspect, the invention provides a use of isolated natural brassinolide analogues of formulae BR6, BR1, BR2, BR3, BR4 and/or BR5 for the promotion of growth and/or stress resistance of a plant; and also provides a use of isolated natural brassinolide analogues of formulae BR6, BR1, BR2, BR3, BR4 and/or BR5 for the preparation of an agricultural composition used in the promotion of growth and/or stress resistance of a plant Preferably in the use of third aspect of the invention, the growth of a plant is selected from development and germination of a plant; and/or, the stress resistance of a plant is selected from resistance to low temperature and salt tolerance of a plant. According to the embodiments of the invention, these excellent properties are embodied in a dicot and/or a monocot.

Preferably in the use of third aspect of the invention, the plant is selected from a dicot and monocot, preferably is selected from rice, wheat, corn, soybean and cotton, more preferably is selected from rice, corn and soybean.

Beneficial effects of the invention are that the process of extraction (purification) is stable; various natural brassinolide analogues with high purity can be collected just by the one extraction method, and shares the cost; various isolated natural brassinolide analogues can be used alone or formulated in a certain proportion, and the quality of the product is stable and easily controlled; the various brassinolide analogues have effects on the promotion of vitality, resistance to low temperature and salt tolerance of a plant, and under certain conditions, their effects and activities were higher than those of chemically synthesized brassinolide products in prior arts.

For a better understanding of the present invention, it will now be described in greater detail by reference to specific drawings and examples. It should be noted that the examples and drawings only exemplify the invention, and should not be construed as limiting the scope of the invention. According to the description of the application, various modifications and alterations of the invention are obvious to a skilled person in the art. The publications cited in the application are used to illustrate the invention, the contents of which are incorporated herein by reference, as if they have been written down herein.

EXAMPLES

Example 1

Extraction and Identification of Natural Brassinolide Analogues 100 g of canola pollens were added to 300 mL of 95% (V/V) ethanol solution. Then the mixture was sonicated and filtered, and the filtrate was retained. The filter residue was added to 300 mL of 95% (V/V) ethanol solution for ultrasonic disruption and filtration, and the filtrate was retained. Both of the filtrate were combined and concentrated to 100 mL by drying at 75° C. and vacuum degree of 0.085 Mpa, and thus the alcohol-soluble pollen extract was obtained.

200 mL of 50% (V/V) ethanol solution were added and mixed into the alcohol-soluble pollen extract. Then 500 mL of ethyl acetate were added to the mixture for extraction, and the upper layer (ethyl acetate layer) was retained. 500 mL of another ethyl acetate were added to the lower layer, and the upper layer (ethyl acetate layer) was retained. Both of the ethyl acetate layers were combined and added to 300 mL of the enzymatic liquid (i.e., the enzymatic mixture of esterase (2500 U/L) and glucoamylase (2000 U/L), in which the esterase and the glucoamylase were purchased from Jining Hemei Bio-Engineering Co., Ltd.). The mixture was stirred (45 rpm) for 1 hr at 40° C. and then dried at 75° C. and vacuum degree of 0.085 Mpa, and thus the ester-soluble extract was obtained.

The ester-soluble extract was loaded on the silica gel chromatographic column (2.6 cm×40 cm, 300 mesh silica gel), and eluted by mobile phase (i.e., the mixture of methanol ethyl acetate, in which the volume ratio of methanol:ethyl acetate is 5:1). When flow rate is 4 ml/min, the eluent eluted from 40th min to 150th min was collected and combined. Then the eluent was dried completely at 75° C. and vacuum degree of 0.085 Mpa, and dissolved in 10 mL of methanol, so the silica gel column-purified liquid was obtained.

Figure 1:
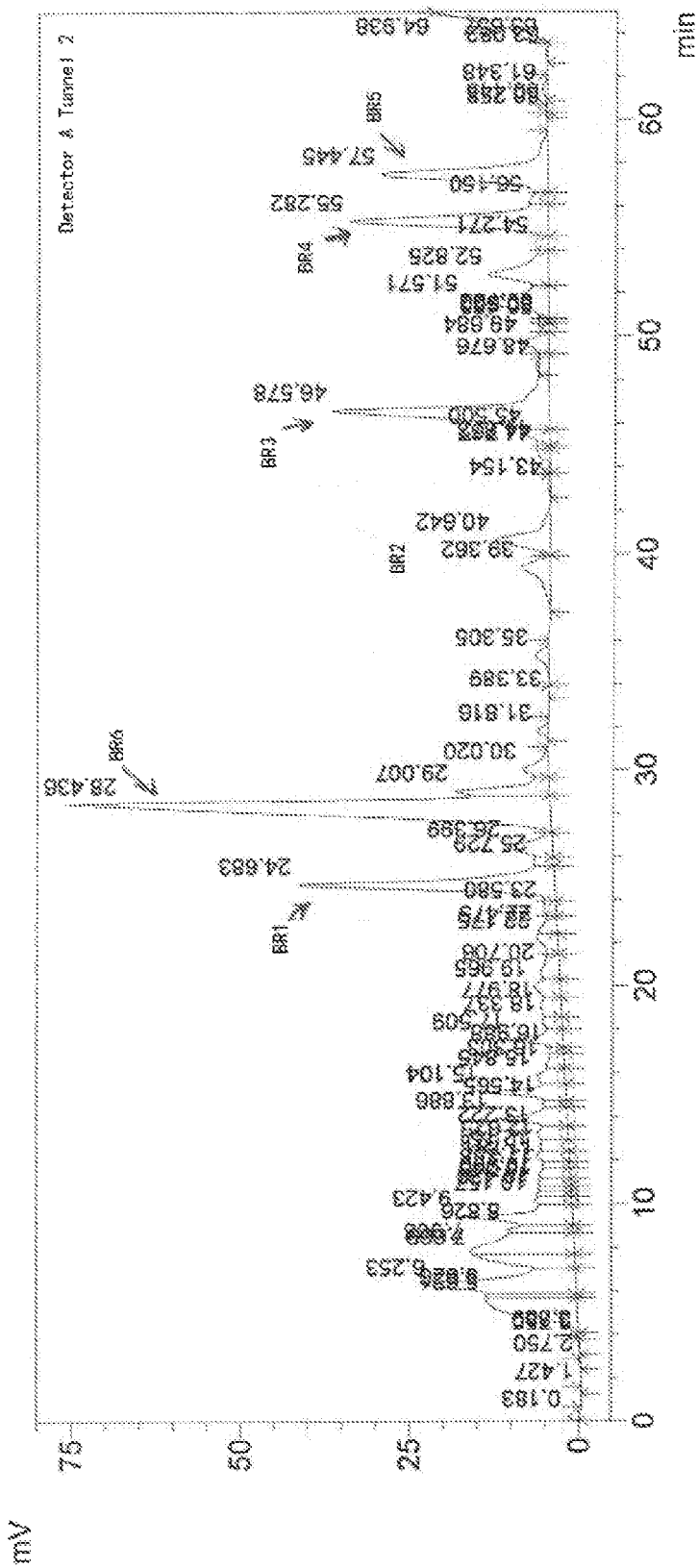
FIG. 1 shows a spectrum of purifying the natural brassinolide analogues.

Then the silica gel column-purified liquid was loaded on the C18 reversed-phase chromatographic column (conditions: 50 mm×25 cm, 5 μm), and eluted by mobile phase (i.e., the mixture of acetonitrile and water, in which the volume ratio of acetonitrile:water is 75:25). When flow rate is 10 ml/min, the elution spectrum is shown as FIG. 1 which indicates every elution peak and time of every natural brassinolide analogues. The natural brassinolide analogues (BR6, BR1, BR2, BR3, BR4, and BR5) were respectively collected at the time of the corresponding elution time. The process mentioned above is stable and produces 6 kinds of the natural brassinolide analogues mentioned above at once, and its overall efficiency is high.

Figure 2:
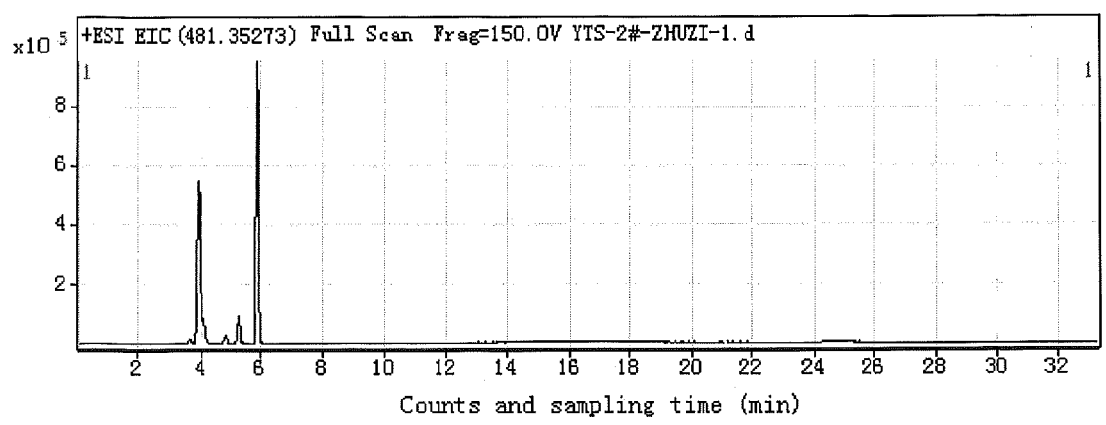
FIG. 2 shows the identification spectra of the natural brassinolide analogues.

The natural brassinolide analogues, BR1, BR2, BR3, BR4, BR5 and BR6, were collected and verified by the high resolution mass spectrometry (the mass spectrum of BR1 is shown as FIG. 2A, that of BR2 is shown as FIG. 2B, that of BR3 is shown as FIG. 2C, that of BR4 is shown as FIG. 2D, that of BR5 is shown as FIG. 2E, and that of BR6 is shown as FIG. 2F). The purity of any one of the analogues was more than 99%. Then according to the standard assays (Mass Spectrometry (GB/T 6041-2002), Infrared Spectroscopy (GB/T6040-2002), Superconducting Pulse Fourier Transform NMR (JY/T 007-1996) and Molecular Absorption Spectrophotometric Analysis (GB/T 9721-2006)), the Analytical Center of Sichuan University was appointed to analyze and resolve the structures of the natural brassinolide analogues as follows:

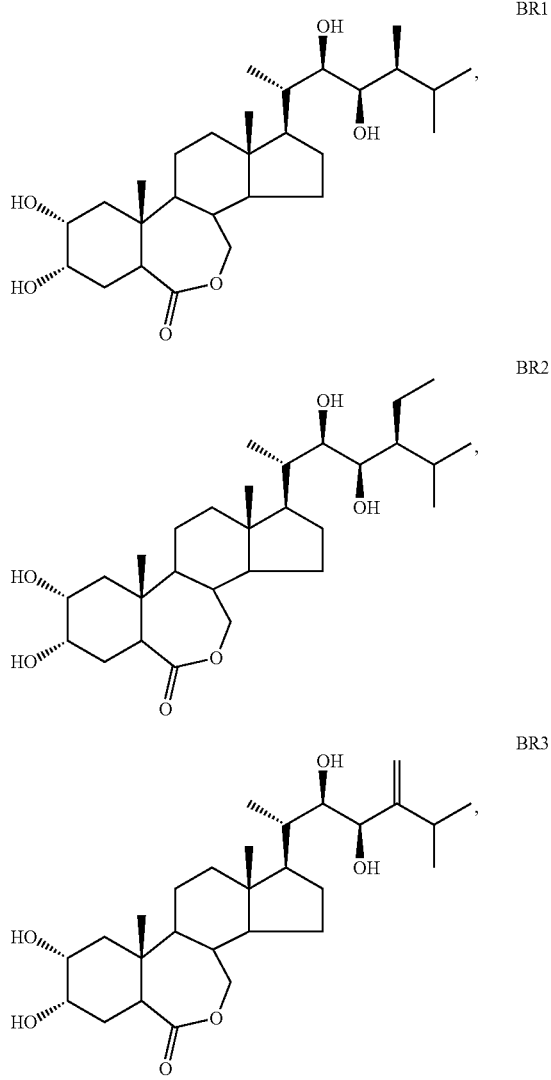

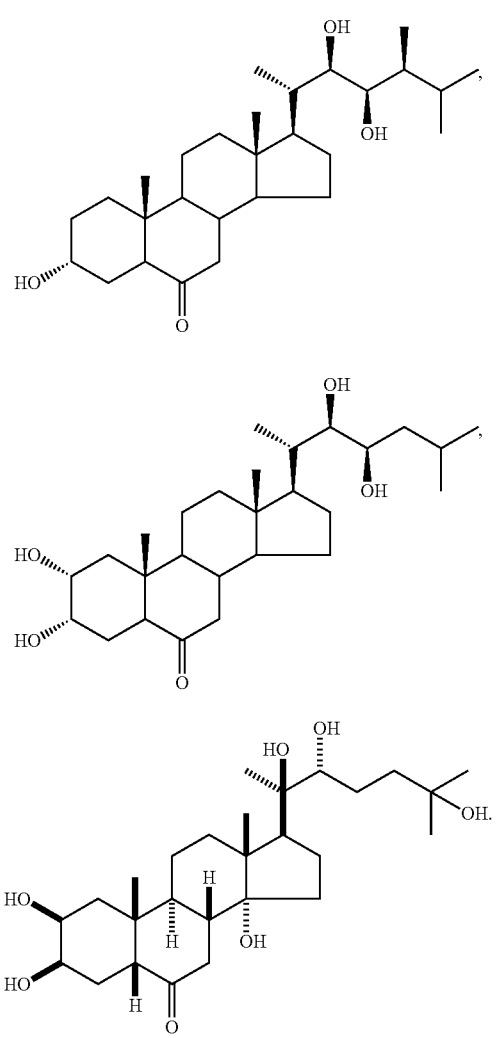

Example 2

Determination of Effects of Natural Brassinolide Analogues on Enhancement of Plant Development According to a rice leaf bending assay, we measured leaf inclination angle of rice to determine effects of the natural brassinolide analogues on the enhancement of plant development. The larger the leaf inclination angle of rice, the more effects on plant development. The detailed assay procedure is as follows:

The natural brassinolide analogues, BR1, BR2, BR3, BR4, BR5 and BR6, used herein, were those prepared by the method of Example 1. And BR1, BR2, BR3, BR4, BR5 and BR6 were mixed into a mixture of brassinolide analogues (referred to as "BRs", in which the weight ratio of BR1:BR2:BR3:BR4:BR5:BR6 is 0.4:0.4:0.4:0.4:0.4:98). Respectively the analogues and the mixture were dissolved into 95% (V/V) ethanol solution, and then diluted with pure water to 1 mg/L, 0.1 mg/L, 0.01 mg/L, 0.001 mg/L and 0.0001 mg/L. In addition, pure water was used as a control.

After rice seeds were disinfected by using 5% sodium hypochlorite solution treatment, they were rinsed with distilled water until their pH>7, placed into a petri dish in a dark incubator, and cultured by using water at 30° C.±2° C. for 9 days. Then the nine-day-old etiolated seedlings of rice were cut around the center of the base of second leaf to segments with 1 cm leaf and 1 cm leaf sheath. The leaf segments were floated in distilled water, placed in a dark incubator, cultured at 30° C.±2° C. for 24 hr, and then dried by a filter paper. The dried leaf segments were respectively immersed in the above solutions containing different concentrations of the natural brassinolide analogues or pure water, and cultured in a dark incubator at 30° C.±2° C. for 48 hr. Every solution or pure water contained the leaf segments from 20 rice. Then the inclination angle between the second leaf and the leaf sheath of the leaf segments was measured by a protractor. The results are shown in table 2-1, which indicate that relative to the control, each of the natural brassinolide analogues or the mixture had significant effects on leaf inclination of rice so as to have effects on plant growth; and substantially the enhancement of the effects was positively correlated to the concentrations of the natural brassinolide analogues and the mixture, while in the case of high concentrations the effects of BR1, BR5, BR6 and BRs are more than those of BR2, BR3 and BR4.

TABLE 2-1

Effects of the Natural Brassinolide Analogues on Rice Leaf Inclination

| Sample | Concentration (mg/l) | Total angle (degree) | Number of rice | Average angle (degree) |
|---|---|---|---|---|
| BR1 | 0.0001 | 106.8 | 20 | 5.34 |
|  | 0.001 | 225.4 | 20 | 11.27 |
|  | 0.01 | 421 | 20 | 21.05 |
|  | 0.1 | 725 | 20 | 36.25 |
|  | 1 | 2215 | 20 | 110.75 |
| BR2 | 0.0001 | 80.5 | 20 | 4.025 |
|  | 0.001 | 145.6 | 20 | 7.28 |
|  | 0.01 | 265 | 20 | 13.25 |
|  | 0.1 | 423 | 20 | 21.15 |
|  | 1 | 1425 | 20 | 71.25 |
| BR3 | 0.0001 | 76.8 | 20 | 3.84 |
|  | 0.001 | 136 | 20 | 6.8 |
|  | 0.01 | 243 | 20 | 12.15 |
|  | 0.1 | 420 | 20 | 21 |
|  | 1 | 1306 | 20 | 65.3 |
| BR4 | 0.0001 | 76 | 20 | 3.8 |
|  | 0.001 | 130 | 20 | 6.5 |
|  | 0.01 | 245 | 20 | 12.25 |
|  | 0.1 | 428 | 20 | 21.4 |
|  | 1 | 1280 | 20 | 64 |
| BR5 | 0.0001 | 78 | 20 | 3.9 |
|  | 0.001 | 186 | 20 | 9.3 |
|  | 0.01 | 401 | 20 | 20.05 |
|  | 0.1 | 700 | 20 | 35 |
|  | 1 | 2200 | 20 | 110 |
| BR6 | 0.0001 | 85 | 20 | 4.25 |
|  | 0.001 | 142 | 20 | 7.1 |
|  | 0.01 | 460 | 20 | 23 |
|  | 0.1 | 710 | 20 | 35.5 |
|  | 1 | 2180 | 20 | 109 |
| BRs | 0.0001 | 70 | 20 | 3.5 |
|  | 0.001 | 125 | 20 | 6.25 |
|  | 0.01 | 430 | 20 | 21.5 |
|  | 0.1 | 690 | 20 | 34.5 |
|  | 1 | 2090 | 20 | 104.5 |
| control |  | 20.5 | 20 | 1.025 |

Example 3

Determination of Effects of Natural Brassinolide Analogues on Resistance to Low Temperature of Plant According to a low temperature assay, we measured parameters including plant height, number of leaf, area of leaf, number of tiller, weight of root at low temperature to completely determine effects of the natural brassinolide analogues on the resistance to low temperature of a plant.

The natural brassinolide analogues, BR1, BR2, BR3, BR4, BR5 and BR6, used herein, were those prepared by the method of Example 1. Respectively the analogues were dissolved into 95% (V/V) ethanol solution, and then diluted with pure water to 1 mg/L, 0.1 mg/L, 0.01 mg/L, 0.001 mg/L and 0.0001 mg/L. In addition, pure water was used as a control.

After rice seeds were disinfected by using 5% sodium hypochlorite solution treatment, they were rinsed with distilled water until their pH>7, placed into a petri dish in a dark incubator, and cultured by using water at 30° C.±2° C. for 9 days. Then respectively the nine-day-old etiolated seedlings of rice were immersed in the above solutions containing different concentrations of the natural brassinolide analogues or pure water, and cultured at the temperature of 1° C., 2° C., 3° C., 4° C. and 5° C. for 24 hr. The parameters including plant height, area of leaf and weight of root after 3, 6, 9 and 12 days and number of leaf and number of tiller after 12 days were measured. The results are shown in tables 3-0~3-6, which indicate that relative to the control, each of the natural brassinolide analogues was capable of increasing height, area of leaf and weight of root of rice at low temperature so as to enhance the resistance to low temperature of a plant; and substantially the enhancement was positively correlated to the concentrations of the natural brassinolide analogues, while the effects of BR1, BR5 and BR6 are more than those of BR2, BR3 and BR4.

TABLE 3-0

Results of Pure Water

| Sample | Concentration (mg/l) | Temperature (° C.) | Height (cm) | Number of leaf | Area of leaf (cm$^2$) | Number of tiller | Weight of root (g) |
|---|---|---|---|---|---|---|---|
| control | | 1 | 6.6/6.7/6.8/7 | 3 | 9.8/11/11.2/12 | 3 | 2.8/3.1/3.3/3.8 |
| | | 2 | 6.6/6.8/6.9/7.1 | 3 | 10/11.1/12/12.3 | 3 | 2.8/3.0/3.2/3.9 |
| | | 3 | 6.8/6.9/6.9/7.2 | 3 | 10.4/12/12.6/13.2 | 2 | 2.5/2.6/2.9/2.9 |
| | | 4 | 6.8/6.9/7.1/7.3 | 3 | 9.6/10.7/11.9/12.4 | 2 | 2.4/2.4/2.5/2.6 |
| | | 5 | 7.0/7.3/7.4/7.7 | 3 | 10.1/11.6/12.4/13 | 2 | 2.4/2.5/2.5/2.7 |

Notes:
data separated by slash are successive data for 3, 6, 9 and 12 days.

TABLE 3-1

Results of Effects of BR1 on Resistance to Low Temperature of Rice

| Sample | Concentration (mg/l) | Temperature (° C.) | Height (cm) | Number of leaf | Area of leaf (cm$^2$) | Number of tiller | Weight of root (g) |
|---|---|---|---|---|---|---|---|
| BR1 | 0.0001 | 1 | 7.1/7.2/7.3/7.4 | 3 | 10/11.2/12.4/13 | 3 | 2.8/3.1/3.4/3.9 |
| | | 2 | 7.1/7.2/7.3/7.5 | 3 | 10.2/11.7/12.6/13 | 3 | 2.8/3.0/3.2/3.9 |
| | | 3 | 7.1/7.2/7.5/7.6 | 3 | 10.4/12/12.6/13.2 | 2 | 2.5/2.6/2.9/2.9 |
| | | 4 | 7.1/7.3/7.5/7.7 | 3 | 10.6/12.2/13/13.4 | 2 | 2.5/2.6/2.9/2.9 |
| | | 5 | 7.2/7.4/7.5/7.8 | 3 | 10.6/12.4/13.6/14 | 2 | 2.6/2.8/2.9/3.0 |
| | 0.001 | 1 | 6.9/7.1/7.3/7.3 | 3 | 10.1/11.3/12.6/13 | 3 | 2.8/3.1/3.4/3.9 |
| | | 2 | 6.9/7.1/7.2/7.3 | 3 | 10.3/11.8/12.6/13.1 | 3 | 2.8/3.0/3.2/3.9 |
| | | 3 | 7/7.1/7.4/7.3 | 3 | 10.4/12/12.6/13.2 | 2 | 2.5/2.6/2.9/2.9 |
| | | 4 | 7.1/7.3/7.5/7.7 | 3 | 10.6/12.4/13.1/13.5 | 2 | 2.5/2.6/2.9/2.9 |
| | | 5 | 7.5/7.7/7.9/8.2 | 3 | 10.7/14.6/16.4/17 | 3 | 2.8/2.9/3.0/3.7 |
| | 0.01 | 1 | 6.9/7.2/7.3/7.4 | 3 | 10.1/11.9/12.9/13.6 | 3 | 2.8/3.0/3.4/3.9 |
| | | 2 | 6.9/7.2/7.3/7.5 | 3 | 10.3/11.8/12.8/13.4 | 3 | 2.8/3.0/3.1/3.2 |
| | | 3 | 7/7.2/7.4/7.6 | 3 | 10.4/12/12.6/13.2 | 2 | 2.5/2.6/2.9/2.9 |
| | | 4 | 7.1/7.3/7.5/7.8 | 3 | 10.8/12.4/13.4/13.7 | 2 | 2.5/2.6/2.9/3.0 |
| | | 5 | 7.7/7.8/8.2/8.5 | 4 | 10.9/13.9/17.4/18 | 3 | 2.8/3.0/3.4/3.9 |
| | 0.1 | 1 | 7.0/7.2/7.3/7.5 | 3 | 10.1/11.9/12.9/13.4 | 3 | 2.8/3.0/3.4/3.6 |
| | | 2 | 7.1/7.2/7.3/7.4 | 3 | 10.4/11.8/12.8/13.6 | 3 | 2.9/3.0/3.1/3.2 |
| | | 3 | 7.2/7.3/7.4/7.6 | 3 | 10.5/12/12.8/13.4 | 2 | 2.5/2.6/2.9/2.9 |
| | | 4 | 7.1/7.4/7.5/7.7 | 3 | 10.8/12.5/13.5/13.8 | 2 | 2.5/2.7/2.9/3.1 |
| | | 5 | 7.7/7.9/8.4/8.7 | 3 | 11.1/13.9/17.8/19 | 2 | 2.9/3.2/3.5/4.1 |
| | 1 | 1 | 7.1/7.2/7.3/7.4 | 3 | 10/11.2/12.4/13 | 3 | 2.8/3.1/3.4/3.9 |
| | | 2 | 7.1/7.2/7.3/7.5 | 3 | 10.2/11.7/12.6/13 | 3 | 2.8/3.0/3.2/3.9 |
| | | 3 | 7.1/7.2/7.5/7.6 | 3 | 10.4/12/12.6/13.2 | 2 | 2.5/2.6/2.9/2.9 |
| | | 4 | 7.1/7.5/7.6/7.7 | 3 | 10.9/12.6/13.7/14 | 2 | 2.5/2.7/3.0/3.2 |
| | | 5 | 7.7/8.0/8.6/8.9 | 3 | 11.1/13.6/18.4/20 | 2 | 2.9/3.5/3.7/4.5 |

Notes:
data separated by slash are successive data for 3, 6, 9 and 12 days.

TABLE 3-2

Results of Effects of BR2 on Resistance to Low Temperature of Rice

| Sample | Concentration (mg/l) | Temperature (° C.) | Height (cm) | Number of leaf | Area of leaf (cm$^2$) | Number of tiller | Weight of root (g) |
|---|---|---|---|---|---|---|---|
| BR2 | 0.0001 | 1 | 6.8/6.9/7/7.2 | 3 | 9.8/11.2/12.4/13.1 | 3 | 2.8/3.1/3.4/3.9 |
|  |  | 2 | 6.8/7/7.1/7.4 | 3 | 10/11.7/12.4/13 | 3 | 2.8/3.0/3.2/3.9 |
|  |  | 3 | 6.9/7.2/7.4/7.5 | 3 | 10/11.8/12.3/13.2 | 2 | 2.5/2.6/2.9/2.9 |
|  |  | 4 | 6.9/7.3/7.5/7.6 | 3 | 10/11.7/13/13.4 | 2 | 2.5/2.6/2.9/2.9 |
|  |  | 5 | 7.0/7.4/7.5/7.7 | 3 | 10.2/12/13.6/14 | 2 | 2.5/2.7/2.9/3.0 |
|  | 0.001 | 1 | 6.9/7.1/7.1/7.3 | 3 | 10.1/11.3/12.6/13 | 3 | 2.8/3.1/3.4/3.9 |
|  |  | 2 | 6.9/7.1/7.1/7.3 | 3 | 9.8/11.6/12.1/13.1 | 3 | 2.8/3.0/3.2/3.9 |
|  |  | 3 | 7/7.1/7.3/7.4 | 3 | 10/12/12.4/13 | 2 | 2.5/2.6/2.9/2.9 |
|  |  | 4 | 7.1/7.3/7.5/7.5 | 3 | 10/12.1/13/13.5 | 2 | 2.5/2.6/2.9/2.9 |
|  |  | 5 | 7.2/7.5/7.8/8 | 3 | 10.2/14/15.4/16 | 3 | 2.8/2.9/3.0/3.7 |
|  | 0.01 | 1 | 7.0/7.2/7.4/7.5 | 3 | 10.1/11.6/12.4/13.6 | 3 | 2.8/3.0/3.4/3.9 |
|  |  | 2 | 7.1/7.2/7.5/7.5 | 3 | 10.1/11.1/12.5/13.4 | 3 | 2.8/3.1/3.1/3.2 |
|  |  | 3 | 7.1/7.2/7.7/7.9 | 3 | 10.2/12/12.6/13.2 | 2 | 2.5/2.6/2.9/2.9 |
|  |  | 4 | 7.1/7.5/7.7/7.8 | 3 | 10.8/12.4/13.2/13.5 | 2 | 2.5/2.6/2.9/3.0 |
|  |  | 5 | 7.4/7.6/8/8.2 | 4 | 10.3/13.1/16.4/17 | 3 | 2.8/3.0/3.4/3.9 |
|  | 0.1 | 1 | 7.0/7.2/7.3/7.4 | 3 | 10.1/11/12.1/13.4 | 3 | 2.8/3.0/3.4/3.6 |
|  |  | 2 | 7.1/7.3/7.3/7.4 | 3 | 10.4/11.2/12.6/13.6 | 3 | 2.8/3.0/3.1/3.2 |
|  |  | 3 | 7.4/7.4/7.8/7.9 | 3 | 10.5/12/12.6/13.4 | 2 | 2.5/2.7/2.9/2.9 |
|  |  | 4 | 7.5/7.5/8/8.1 | 3 | 10.8/12.1/13.4/13.8 | 2 | 2.5/2.7/2.9/3.1 |
|  |  | 5 | 7.5/7.6/8.1/8.3 | 3 | 11/12.9/16.8/19 | 2 | 2.9/3.2/3.5/4.1 |
|  | 1 | 1 | 7.2/7.3/7.3/7.9 | 3 | 10/11.2/12.4/13 | 3 | 2.6/3.1/3.2/3.7 |
|  |  | 2 | 7.2/7.2/7.3/8 | 3 | 10.2/11.7/12.6/13 | 3 | 2.6/3.0/3.2/3.7 |
|  |  | 3 | 7.4/7.5/7.9/8.1 | 3 | 10.4/12/12.1/13.2 | 2 | 2.5/2.6/2.9/2.9 |
|  |  | 4 | 7.4/7.5/8.0/8.2 | 3 | 10.9/12.6/13.2/14 | 2 | 2.5/2.7/3.0/3.2 |
|  |  | 5 | 7.4/7.7/8.2/8.4 | 3 | 11.1/13.1/18/20 | 2 | 2.9/3.5/3.7/4.5 |

Notes:
data separated by slash are successive data for 3, 6, 9 and 12 days.

TABLE 3-3

Results of Effects of BR3 on Resistance to Low Temperature of Rice

| Sample | Concentration (mg/l) | Temperature (° C.) | Height (cm) | Number of leaf | Area of leaf (cm$^2$) | Number of tiller | Weight of root (g) |
|---|---|---|---|---|---|---|---|
| BR3 | 0.0001 | 1 | 6.8/6.9/7.1/7.2 | 3 | 9.8/11/12.2/13.1 | 3 | 2.8/3/3.4/3.9 |
|  |  | 2 | 6.8/7/7.1/7.4 | 3 | 10/11.7/12.1/13 | 3 | 2.8/3.0/3.2/3.9 |
|  |  | 3 | 6.9/7.1/7.4/7.5 | 3 | 10/11.8/12.1/13.2 | 2 | 2.5/2.6/2.9/2.9 |
|  |  | 4 | 6.9/7.3/7.5/7.5 | 3 | 10/11.5/13/13.4 | 2 | 2.5/2.6/2.9/2.9 |
|  |  | 5 | 7.0/7.4/7.5/7.7 | 3 | 10.2/12/13.4/14 | 2 | 2.5/2.5/2.9/3.0 |
|  | 0.001 | 1 | 6.9/7.1/7.1/7.3 | 3 | 10/11.3/12.6/13 | 3 | 2.8/3.1/3.2/3.9 |
|  |  | 2 | 6.9/7.1/7.1/7.3 | 3 | 9.8/11.6/12/13.1 | 3 | 2.8/3.0/3.1/3.9 |
|  |  | 3 | 7/7.2/7.3/7.4 | 3 | 10/12/12.2/13 | 2 | 2.5/2.7/2.9/2.9 |
|  |  | 4 | 7.1/7.3/7.4/7.5 | 3 | 10/12/13/13.1 | 2 | 2.5/2.6/2.9/2.9 |
|  |  | 5 | 7.2/7.5/7.8/7.9 | 3 | 10.2/14/15.4/16 | 3 | 2.8/2.9/3.0/3.7 |
|  | 0.01 | 1 | 7.0/7.1/7.4/7.5 | 3 | 10/11.6/12.4/13.6 | 3 | 2.8/3.0/3.1/3.9 |
|  |  | 2 | 7.1/7.2/7.4/7.5 | 3 | 10.1/11/12.5/13.4 | 3 | 2.8/3.1/3/3.2 |
|  |  | 3 | 7.1/7.3/7.5/7.8 | 3 | 10.2/12/12.1/13.2 | 2 | 2.5/2.7/2.9/2.9 |
|  |  | 4 | 7.1/7.4/7.7/7.8 | 3 | 10.8/12.4/13/13.5 | 2 | 2.5/2.6/2.9/3.0 |
|  |  | 5 | 7.4/7.6/7.8/8.2 | 4 | 10.3/13.1/16.4/17 | 3 | 2.8/3.0/3.4/3.9 |
|  | 0.1 | 1 | 7.1/7.2/7.3/7.4 | 3 | 10.1/11/12.1/13.1 | 3 | 2.8/2.9/3.4/3.6 |
|  |  | 2 | 7.1/7.3/7.3/7.4 | 3 | 10.4/11.2/12.6/13.2 | 3 | 2.8/3.0/3/3.2 |
|  |  | 3 | 7.3/7.4/7.8/7.9 | 3 | 10.5/12/12.1/13.4 | 2 | 2.5/2.7/2.7/2.9 |
|  |  | 4 | 7.4/7.4/7.8/8.1 | 3 | 10.8/12/13.4/13.4 | 2 | 2.5/2.7/2.9/3.1 |
|  |  | 5 | 7.5/7.5/8/8.1 | 3 | 11/12.1/16.2/17.9 | 2 | 2.9/3.2/3.5/4.1 |
|  | 1 | 1 | 7.2/7.2/7.3/7.9 | 3 | 10/11/12.4/13 | 3 | 2.6/3.1/3.1/3.7 |
|  |  | 2 | 7.2/7.2/7.4/8 | 3 | 10.2/11.7/12/13 | 3 | 2.6/3.0/3.2/3.7 |
|  |  | 3 | 7.4/7.5/7.7/8.1 | 3 | 10.4/12/12/13.2 | 2 | 2.5/2.6/2.7/2.9 |
|  |  | 4 | 7.4/7.5/7.8/8.2 | 3 | 10.9/12/13.2/14 | 2 | 2.5/2.7/3.0/3.2 |
|  |  | 5 | 7.4/7.5/8.2/8.3 | 3 | 11.1/13.1/18/20 | 2 | 2.9/3.5/3.7/4.5 |

Notes:
data separated by slash are successive data for 3, 6, 9 and 12 days.

TABLE 3-4

Results of Effects of BR4 on Resistance to Low Temperature of Rice

| Sample | Concentration (mg/l) | Temperature (° C.) | Height (cm) | Number of leaf | Area of leaf (cm$^2$) | Number of tiller | Weight of root (g) |
|---|---|---|---|---|---|---|---|
| BR4 | 0.0001 | 1 | 6.8/6.9/7/7.2 | 3 | 9.8/11/12.2/13 | 3 | 2.8/3/3.1/3.5 |
| | | 2 | 6.8/7/7.1/7.2 | 3 | 10/11.7/12/13 | 3 | 2.8/3.0/3.2/3.7 |
| | | 3 | 6.9/7.1/7.4/7.4 | 3 | 10/11.8/12.1/13 | 2 | 2.5/2.6/2.9/2.9 |
| | | 4 | 6.9/7.1/7.5/7.5 | 3 | 10/11.5/13/13.4 | 2 | 2.5/2.6/2.9/2.9 |
| | | 5 | 7.0/7.3/7.5/7.6 | 3 | 10.2/12/13/13.4 | 2 | 2.5/2.5/2.9/2.9 |
| | 0.001 | 1 | 6.9/7/7.1/7.4 | 3 | 10/11.3/12.6/13.6 | 3 | 2.8/3.1/3.2/3.7 |
| | | 2 | 6.9/7/7.1/7.3 | 3 | 9.8/11.6/12/13.1 | 3 | 2.8/3.0/3/3.9 |
| | | 3 | 7/7.2/7.4/7.5 | 3 | 10/12/12.2/13 | 2 | 2.5/2.6/2.9/2.9 |
| | | 4 | 7.1/7.3/7.4/7.5 | 3 | 10/12/13/13.1 | 2 | 2.5/2.6/2.9/2.9 |
| | | 5 | 7.2/7.4/7.4/7.9 | 3 | 10.2/14/15.4/16 | 3 | 2.8/2.9/3.0/3.7 |
| | 0.01 | 1 | 6.7/7.1/7.4/7.5 | 3 | 9.2/11.6/12.4/13.6 | 3 | 2.8/3.0/3.1/3.9 |
| | | 2 | 7/7.2/7.4/7.5 | 3 | 10/11/12.5/13.4 | 3 | 2.8/3/3/3.2 |
| | | 3 | 7/7.3/7.5/7.8 | 3 | 10.2/12/12.1/13.2 | 2 | 2.5/2.6/2.9/2.9 |
| | | 4 | 7/7.4/7.7/7.8 | 3 | 10.8/12.4/13/13.5 | 2 | 2.5/2.7/2.9/3.0 |
| | | 5 | 7.2/7.6/7.8/8.2 | 4 | 10.3/13.1/16.4/17 | 3 | 2.8/3.0/3.4/3.9 |
| | 0.1 | 1 | 7.1/7.2/7.3/7.3 | 3 | 10/11/12.1/13.1 | 3 | 2.8/2.9/3.3/3.6 |
| | | 2 | 7.1/7.1/7.3/7.4 | 3 | 10.2/11.2/12.6/13.2 | 3 | 2.8/3.1/3.1/3.2 |
| | | 3 | 7.3/7.4/7.8/7.9 | 3 | 10.5/12/12.1/13.4 | 2 | 2.5/2.7/2.7/2.9 |
| | | 4 | 7.3/7.4/7.8/8 | 3 | 10.6/12/13.2/13.4 | 2 | 2.5/2.6/2.9/3.1 |
| | | 5 | 7.4/7.5/8/8.1 | 3 | 11/12.1/16.2/17.8 | 2 | 2.9/3.1/3.5/4.1 |
| | 1 | 1 | 6.8/7/7.1/7.7 | 3 | 10/11/12.4/13 | 3 | 2.6/3.1/3.2/3.7 |
| | | 2 | 7/7.2/7.4/8 | 3 | 10.1/11.7/12/13 | 3 | 2.55/3.0/3.2/3.7 |
| | | 3 | 7/7.5/7.7/8.1 | 3 | 10.4/12/12/13.2 | 2 | 2.5/2.6/2.6/2.9 |
| | | 4 | 7.3/7.5/7.8/8.2 | 3 | 10.7/12/13.2/14 | 2 | 2.5/2.7/3.0/3.2 |
| | | 5 | 7.4/7.4/8.1/8.3 | 3 | 11.1/13/18/20 | 2 | 2.9/3.5/3.7/4.5 |

Notes:
data separated by slash are successive data for 3, 6, 9 and 12 days.

TABLE 3-5

Results of Effects of BR5 on Resistance to Low Temperature of Rice

| Sample | Concentration (mg/l) | Temperature (° C.) | Height (cm) | Number of leaf | Area of leaf (cm$^2$) | Number of tiller | Weight of root (g) |
|---|---|---|---|---|---|---|---|
| BR5 | 0.0001 | 1 | 6.8/6.9/7/7.2 | 3 | 9.8/11.2/12/13.1 | 3 | 2.8/3.1/3.4/3.6 |
| | | 2 | 6.8/7/7.1/7.4 | 3 | 10/11.7/12.4/13 | 3 | 2.8/3.0/3.2/3.4 |
| | | 3 | 6.9/7.2/7.4/7.5 | 3 | 10/11.8/12.3/13.2 | 2 | 2.5/2.6/2.9/2.9 |
| | | 4 | 6.9/7.3/7.5/7.6 | 3 | 10/11.7/13/13.4 | 2 | 2.5/2.6/2.7/2.9 |
| | | 5 | 7.0/7.2/7.5/7.7 | 3 | 10.2/12/13.2/14 | 2 | 2.5/2.7/2.9/3.0 |
| | 0.001 | 1 | 6.9/7.1/7.2/7.3 | 3 | 10.1/11.3/12.8/13 | 3 | 2.8/3.1/3.3/3.9 |
| | | 2 | 6.9/7.1/7.3/7.3 | 3 | 9.8/11.6/12.2/13.1 | 3 | 2.8/3.0/3.2/3.9 |
| | | 3 | 7/7/7.3/7.4 | 3 | 10/12/12.4/13 | 2 | 2.5/2.6/2.9/2.9 |
| | | 4 | 7.1/7.3/7.5/7.5 | 3 | 10/12.1/13/13.5 | 2 | 2.5/2.6/2.9/2.9 |
| | | 5 | 7.2/7.5/7.6/8 | 3 | 10.2/14/15.4/16 | 3 | 2.8/2.9/3.0/3.4 |
| | 0.01 | 1 | 7.0/7.2/7.3/7.5 | 3 | 10.1/11.6/12/13.6 | 3 | 2.8/3.0/3.1/3.9 |
| | | 2 | 7.1/7.2/7.5/7.5 | 3 | 10.1/11.1/12.1/13.4 | 3 | 2.8/3/3/3.2 |
| | | 3 | 7.1/7.2/7.5/7.9 | 3 | 10.2/12/12.2/13.2 | 2 | 2.5/2.6/2.7/2.9 |
| | | 4 | 7.1/7.5/7.6/7.8 | 3 | 10.8/12.4/13.1/13.5 | 2 | 2.5/2.6/2.9/3.0 |
| | | 5 | 7.4/7.4/8/8.2 | 4 | 10.3/13.1/16.4/17 | 3 | 2.8/3.0/3.4/3.6 |
| | 0.1 | 1 | 7.0/7.2/7.2/7.4 | 3 | 10.1/11/12/13.4 | 3 | 2.8/3.0/3.4/3.4 |
| | | 2 | 7.1/7.3/7.3/7.4 | 3 | 10.4/11.2/12.4/13.6 | 3 | 2.8/3.0/3.1/3.2 |
| | | 3 | 7.4/7.4/7.9/7.9 | 3 | 10.5/12/12.6/13.4 | 2 | 2.5/2.7/2.7/2.9 |
| | | 4 | 7.5/7.5/8/8 | 3 | 10.8/12.1/13.2/13.8 | 2 | 2.5/2.7/2.9/3 |
| | | 5 | 7.5/7.6/8/8.3 | 3 | 11/12.9/16.8/19 | 2 | 2.9/3.2/3.5/4.1 |
| | 1 | 1 | 7.0/7.3/7.3/7.9 | 3 | 10/11.2/12.4/13.7 | 3 | 2.6/3.1/3.1/3.7 |
| | | 2 | 7.1/7.2/7.2/7.8 | 3 | 10.2/11.7/12.6/12.8 | 3 | 2.6/3.0/3.2/3.7 |
| | | 3 | 7.2/7.5/7.6/8.1 | 3 | 10.4/12/12.1/13 | 2 | 2.5/2.6/2.8/2.9 |
| | | 4 | 7.2/7.5/7.8/8.2 | 3 | 10.9/12.6/13.2/13.4 | 2 | 2.5/2.7/3.1/3.2 |
| | | 5 | 7.3/7.7/8/8.4 | 3 | 11.1/13.1/18/20 | 2 | 2.9/3.5/3.6/4.5 |

Notes:
data separated by slash are successive data for 3, 6, 9 and 12 days.

TABLE 3-6

Results of Effects of BR6 on Resistance to Low Temperature of Rice

| Sample | Concentration (mg/l) | Temperature (° C.) | Height (cm) | Number of leaf | Area of leaf (cm$^2$) | Number of tiller | Weight of root (g) |
|---|---|---|---|---|---|---|---|
| BR6 | 0.0001 | 1 | 7.1/7.2/7.4/7.4 | 3 | 10/11.2/12.4/13 | 3 | 2.8/3.1/3.5/3.9 |
| | | 2 | 7.1/7.2/7.3/7.5 | 3 | 10.2/11.7/12.6/13 | 3 | 2.8/3.0/3.2/3.9 |
| | | 3 | 7.1/7.2/7.5/7.6 | 3 | 10.4/12/12.6/13.2 | 2 | 2.5/2.6/2.9/2.9 |
| | | 4 | 7.1/7.3/7.5/7.7 | 3 | 10.6/12.2/13/13.4 | 2 | 2.5/2.6/2.8/2.9 |
| | | 5 | 7.2/7.5/7.5/7.8 | 3 | 10.6/12.8/13.6/14 | 2 | 2.6/2.7/2.9/3.0 |
| | 0.001 | 1 | 6.9/7.1/7.3/7.3 | 3 | 10/11.3/12.6/13 | 3 | 2.8/3.1/3.4/3.9 |
| | | 2 | 6.9/7.1/7.2/7.3 | 3 | 10.3/11.8/12.7/13.1 | 3 | 2.8/3.0/3.2/3.9 |
| | | 3 | 7/7.1/7.4/7.4 | 3 | 10.4/12/12.6/13.2 | 2 | 2.5/2.6/2.9/2.9 |
| | | 4 | 7.1/7.3/7.5/7.7 | 3 | 10.6/12.4/13.1/13.5 | 2 | 2.5/2.6/2.9/2.9 |
| | | 5 | 7.5/7.8/7.9/8.2 | 3 | 10.7/14.6/16/17 | 3 | 2.8/2.7/3.0/3.7 |
| | 0.01 | 1 | 7.0/7.2/7.3/7.4 | 3 | 10/11.9/12.9/13.6 | 3 | 2.8/3.0/3.4/3.9 |
| | | 2 | 7.0/7.2/7.3/7.5 | 3 | 10.6/11.8/12.8/13.4 | 3 | 2.8/3.0/3.1/3.2 |
| | | 3 | 7/7.2/7.4/7.6 | 3 | 10.4/12/12.6/13.2 | 2 | 2.5/2.6/2.9/2.9 |
| | | 4 | 7.1/7.3/7.6/7.8 | 3 | 10.8/12.4/13.7/13.7 | 2 | 2.5/2.6/2.9/3.0 |
| | | 5 | 7.7/7.8/8.1/8.5 | 4 | 10.9/13.9/17.1/18 | 3 | 2.8/3.0/3.4/3.9 |
| | 0.1 | 1 | 7.0/7.3/7.3/7.5 | 3 | 10.1/12/12.9/13.4 | 3 | 2.8/3.0/3.4/3.7 |
| | | 2 | 7.1/7.2/7.3/7.4 | 3 | 10.4/11.8/12.8/13 | 3 | 2.9/3.0/3.1/3.2 |
| | | 3 | 7.2/7.3/7.4/7.5 | 3 | 10.5/12/12.8/13.2 | 2 | 2.5/2.6/2.8/2.9 |
| | | 4 | 7.1/7.4/7.5/7.7 | 3 | 10.8/12.5/13.5/13.8 | 2 | 2.5/2.7/2.9/3.1 |
| | | 5 | 7.7/7.8/8.4/8.6 | 3 | 11.1/13.9/17.8/18.9 | 2 | 2.9/3.2/3.5/4 |
| | 1 | 1 | 7.1/7.2/7.3/7.3 | 3 | 10/11.2/12.4/12.8 | 3 | 2.8/3.1/3.4/3.9 |
| | | 2 | 7.1/7.2/7.3/7.6 | 3 | 10.2/11.7/12.6/13.1 | 3 | 2.8/3.0/3.2/3.9 |
| | | 3 | 7.1/7.3/7.5/7.6 | 3 | 10.4/12.2/12.6/13.2 | 2 | 2.5/2.6/2.9/2.9 |
| | | 4 | 7.1/7.5/7.5/7.7 | 3 | 10.9/12/13.4/14 | 2 | 2.5/2.6/3.0/3.2 |
| | | 5 | 7.7/8.0/8.8/8.9 | 3 | 11.1/13.6/18.9/20 | 2 | 2.9/3.6/3.7/4.5 |

Notes:
data separated by slash are successive data for 3, 6, 9 and 12 days.

Example 4

Determination of Effects of Natural Brassinolide Analogues on Salt Tolerance of Plant According to a salt tolerance assay, we measured germination of rice seed under high salt environment to determine effects of the natural brassinolide analogues on the salt tolerance of a plant.

The natural brassinolide analogues, BR1, BR2, BR3, BR4, BR5 and BR6, used herein, were those prepared by the method of Example 1. And BR1, BR2, BR3, BR4, BR5 and BR6 were mixed into a mixture of brassinolide analogues (referred to as "BRs", in which the weight ratio of BR1:BR2:BR3:BR4:BR5:BR6 is 0.4:0.4:0.4:0.4:0.4:98). Respectively the analogues and the mixture were dissolved into 95% (V/V) ethanol solution, and then diluted with pure water to 1 mg/L, 0.1 mg/L, 0.01 mg/L, 0.001 mg/L and 0.0001 mg/L. In addition, pure water was used as a control. Furthermore, NaCl was added to the above solutions containing different concentrations of the natural brassinolide analogues or pure water respectively, and the concentrations of the salt are 300, 400, 500 and 600 mg/L respectively.

After rice seeds were disinfected by using 5% sodium hypochlorite solution treatment, they were rinsed with distilled water until their pH>7, placed into a petri dish in a dark incubator, and cultured at 30° C.±2° C. by using the above solutions containing different concentrations of the natural brassinolide analogues or pure water for observing the germination and calculating germination rates. The results are shown in tables 4-0~4-4, which indicate that relative to the control, each of the natural brassinolide analogues and the mixture were capable of increasing germination rates of rice under high salt environment so as to enhance the salt tolerance of a plant; and substantially the enhancement of the germination rates was positively correlated to the concentrations of the natural brassinolide analogues and the mixture.

TABLE 4-0

Results of Pure Water

| Sample | Concentration of salt (mg/l) | Germination rate (%) |
|---|---|---|
| control | 300 | 45 |
| | 400 | 42 |
| | 500 | 37 |
| | 600 | 31 |

TABLE 4-1

Results of Effects of BR1 and BR2 on Salt Tolerance of Rice

| Sample | Concentration of sample (mg/l) | Concentration of salt (mg/l) | Germination rate (%) |
|---|---|---|---|
| BR1 | 0.0001 | 300 | 51 |
| | | 400 | 48 |
| | | 500 | 42 |
| | | 600 | 36 |
| | 0.001 | 300 | 53 |
| | | 400 | 49 |
| | | 500 | 45 |
| | | 600 | 37 |
| | 0.01 | 300 | 55 |
| | | 400 | 52 |
| | | 500 | 47 |
| | | 600 | 39 |
| | 0.1 | 300 | 58 |
| | | 400 | 52 |
| | | 500 | 49 |
| | | 600 | 40 |
| | 1 | 300 | 62 |
| | | 400 | 55 |

TABLE 4-1-continued

Results of Effects of BR1 and BR2 on Salt Tolerance of Rice

| Sample | Concentration of sample (mg/l) | Concentration of salt (mg/l) | Germination rate (%) |
|---|---|---|---|
|  |  | 500 | 50 |
|  |  | 600 | 42 |
| BR2 | 0.0001 | 300 | 45 |
|  |  | 400 | 41 |
|  |  | 500 | 39 |
|  |  | 600 | 36 |
|  | 0.001 | 300 | 50 |
|  |  | 400 | 42 |
|  |  | 500 | 40 |
|  |  | 600 | 36 |
|  | 0.01 | 300 | 50 |
|  |  | 400 | 51 |
|  |  | 500 | 47 |
|  |  | 600 | 39 |
|  | 0.1 | 300 | 50 |
|  |  | 400 | 50 |
|  |  | 500 | 46 |
|  |  | 600 | 38 |
|  | 1 | 300 | 58 |
|  |  | 400 | 51 |
|  |  | 500 | 46 |
|  |  | 600 | 38 |

TABLE 4-2

Results of Effects of BR3 and BR4 on Salt Tolerance of Rice

| Sample | Concentration of sample (mg/l) | Concentration of salt (mg/l) | Germination rate (%) |
|---|---|---|---|
| BR3 | 0.0001 | 300 | 50 |
|  |  | 400 | 45 |
|  |  | 500 | 39 |
|  |  | 600 | 32 |
|  | 0.001 | 300 | 50 |
|  |  | 400 | 43 |
|  |  | 500 | 40 |
|  |  | 600 | 33 |
|  | 0.01 | 300 | 51 |
|  |  | 400 | 50 |
|  |  | 500 | 47 |
|  |  | 600 | 39 |
|  | 0.1 | 300 | 50 |
|  |  | 400 | 50 |
|  |  | 500 | 41 |
|  |  | 600 | 38 |
|  | 1 | 300 | 52 |
|  |  | 400 | 46 |
|  |  | 500 | 40 |
|  |  | 600 | 38 |
| BR4 | 0.0001 | 300 | 50 |
|  |  | 400 | 47 |
|  |  | 500 | 42 |
|  |  | 600 | 36 |
|  | 0.001 | 300 | 51 |
|  |  | 400 | 49 |
|  |  | 500 | 43 |
|  |  | 600 | 37 |
|  | 0.01 | 300 | 55 |
|  |  | 400 | 52 |
|  |  | 500 | 47 |
|  |  | 600 | 39 |
|  | 0.1 | 300 | 58 |
|  |  | 400 | 50 |
|  |  | 500 | 49 |
|  |  | 600 | 40 |

TABLE 4-2-continued

Results of Effects of BR3 and BR4 on Salt Tolerance of Rice

| Sample | Concentration of sample (mg/l) | Concentration of salt (mg/l) | Germination rate (%) |
|---|---|---|---|
|  | 1 | 300 | 60 |
|  |  | 400 | 55 |
|  |  | 500 | 50 |
|  |  | 600 | 41 |

TABLE 4-3

Results of Effects of BR5 and BR6 on Salt Tolerance of Rice

| Sample | Concentration of sample (mg/l) | Concentration of salt (mg/l) | Germination rate (%) |
|---|---|---|---|
| BR5 | 0.0001 | 300 | 50 |
|  |  | 400 | 48 |
|  |  | 500 | 42 |
|  |  | 600 | 36 |
|  | 0.001 | 300 | 52 |
|  |  | 400 | 49 |
|  |  | 500 | 45 |
|  |  | 600 | 38 |
|  | 0.01 | 300 | 56 |
|  |  | 400 | 51 |
|  |  | 500 | 47 |
|  |  | 600 | 39 |
|  | 0.1 | 300 | 58 |
|  |  | 400 | 52 |
|  |  | 500 | 43 |
|  |  | 600 | 40 |
|  | 1 | 300 | 62 |
|  |  | 400 | 55 |
|  |  | 500 | 50 |
|  |  | 600 | 42 |
| BR6 | 0.0001 | 300 | 52 |
|  |  | 400 | 48 |
|  |  | 500 | 42 |
|  |  | 600 | 36 |
|  | 0.001 | 300 | 53 |
|  |  | 400 | 50 |
|  |  | 500 | 44 |
|  |  | 600 | 37 |
|  | 0.01 | 300 | 55 |
|  |  | 400 | 51 |
|  |  | 500 | 46 |
|  |  | 600 | 39 |
|  | 0.1 | 300 | 58 |
|  |  | 400 | 53 |
|  |  | 500 | 47 |
|  |  | 600 | 42 |
|  | 1 | 300 | 68 |
|  |  | 400 | 55 |
|  |  | 500 | 52 |
|  |  | 600 | 44 |

TABLE 4-4

Results of Effects of BRs on Salt Tolerance of Rice

| Sample | Concentration of sample (mg/l) | Concentration of salt (mg/l) | Germination rate (%) |
|---|---|---|---|
| BRs | 0.0001 | 300 | 51 |
|  |  | 400 | 46 |
|  |  | 500 | 43 |
|  |  | 600 | 36 |
|  | 0.001 | 300 | 54 |
|  |  | 400 | 50 |

TABLE 4-4-continued

Results of Effects of BRs on Salt Tolerance of Rice

| Sample | Concentration of sample (mg/l) | Concentration of salt (mg/l) | Germination rate (%) |
|---|---|---|---|
|  |  | 500 | 44 |
|  |  | 600 | 37 |
|  | 0.01 | 300 | 55 |
|  |  | 400 | 52 |
|  |  | 500 | 47 |
|  |  | 600 | 39 |
|  | 0.1 | 300 | 58 |
|  |  | 400 | 54 |
|  |  | 500 | 49 |
|  |  | 600 | 42 |
|  | 1 | 300 | 64 |
|  |  | 400 | 57 |
|  |  | 500 | 50 |
|  |  | 600 | 44 |

Example 5

Determination of Effects of Mixture of Natural Brassinolide Analogues and Chemically Synthesized Brassinolide in Farmland BR1, BR2, BR3, BR4, BR5 and BR6 were mixed into a mixture of brassinolide analogues (referred to as "BRs", in which the weight ratio of BR1:BR2:BR3:BR4:BR5:BR6 is 0.4:0.4:0.4:0.4:0.4:98). pure water was used as a negative control, while chemically synthesized homobrassinolide (purchased from Yunda Technology Co., Ltd.) was used as a positive control. Respectively BRs and the positive control were diluted to the concentrations of 1 ppm, 0.5 ppm, 0.1 ppm, 0.05 ppm, 0.01 ppm, 0.005 ppm, 0.001 ppm, 0.0005 ppm and 0.0001 ppm. The subjects for the experimentation are soybean seeds in an experimental farmland. We sowed the soybean seeds on 9th July, surveyed the germination on 22nd July, 23rd July and 24th July, and measured the height on 5th September 5.

The results are shown in table 5-1, which indicate that relative to the negative control, both of homobrassinolide or the mixture of brassinolide analogues from natural source of the invention had positive and different effects on germination, height, fresh weight and dry weight of soybean. In the case of low concentration, substantially all effects of BRs of the invention on soybean growth were better those of the chemically synthesized product of prior art. For example, as shown in table 5-1, the effects of 0.005 ppm of BRs of the invention were even better than those of 0.01 ppm of the chemically synthesized homobrassinolide.

TABLE 5-1

Results of Effects of Brassinolides on Soybean

| Sample | Concentration (ppm) | Number of Seedling (per plant) | Germination rate (%) | Height (cm) | Fresh weight (g/per plant) | Dry weight (g/per plant) |
|---|---|---|---|---|---|---|
| BRs | 0.1 | 114 | 57 | 17.20 | 3.79 | 0.42 |
|  | 0.05 | 118 | 62.1 | 17.95 | 4.08 | 0.45 |
|  | 0.01 | 129 | 64.5 | 17.82 | 4.07 | 0.44 |
|  | 0.005 | 125 | 62.5 | 17.65 | 4.05 | 0.40 |
|  | 0.001 | 119 | 59.5 | 17.44 | 4.02 | 0.38 |
|  | 0.0005 | 112 | 58.6 | 17.23 | 3.99 | 0.38 |
|  | 0.0001 | 100 | 54.3 | 17.14 | 3.97 | 0.35 |
| positive control | 0.1 | 106 | 53 | 17.14 | 3.89 | 0.41 |
|  | 0.05 | 115 | 57.5 | 17.32 | 4.05 | 0.39 |
|  | 0.01 | 121 | 60.5 | 17.19 | 4.01 | 0.40 |
|  | 0.005 | 118 | 59 | 17.08 | 3.98 | 0.39 |
|  | 0.001 | 113 | 56.5 | 17.09 | 3.95 | 0.35 |
|  | 0.0005 | 98 | 52.4 | 17.02 | 3.94 | 0.33 |
|  | 0.0001 | 95 | 47.5 | 16.98 | 3.94 | 0.34 |
| negative control |  | 97 | 48.5 | 16.98 | 3.94 | 0.33 |

The invention claimed is:

1. An extraction method of natural brassinolide analogues, comprising the steps of:
  (1) extracting crushed canola pollens by using 80-100% (V/V) aqueous ethanol solution, and retaining filtrate after solid-liquid separation, optionally further concentrating the filtrate, for obtaining an alcohol-soluble liquid extract;
  (2) mixing the alcohol-soluble liquid extract and 0-60% (V/V) aqueous ethanol solution, then adding ethyl acetate for extraction, retaining ethyl acetate layer, adding esterase and glucoamylase to the layer for an incomplete reaction, and then drying the layer, for obtaining an ester-soluble extract, wherein the incomplete reaction is a reaction at 35-42° C. for 0.5-2 hours and terminated before an enzyme converts all of the substrate and resulting in diversity of natural brassinolide analogues, the esterase is an esterase exacted from a bacterium, and the glucoamylase is a glucoamylase extracted from a fungus;
  (3) loading the ester-soluble extract on a silica gel chromatographic column, eluting by using a mixture of methanol and ethyl acetate, collecting eluent comprising natural brassinolide analogues, drying and dissolving the eluent into methanol, for obtaining a silica gel column-purified liquid; and
  (4) loading the silica gel column-purified liquid on a C18 reversed-phase chromatographic column, eluting by using a mixture of acetonitrile and water, respectively collecting eluent comprising natural brassinolide analogues of formulae BR6, BR1, BR2, BR3, BR4 and/or BR5:

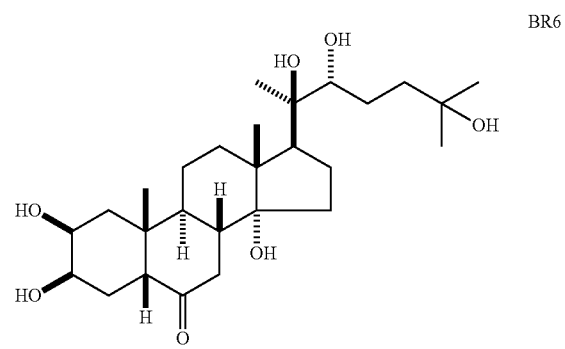

-continued

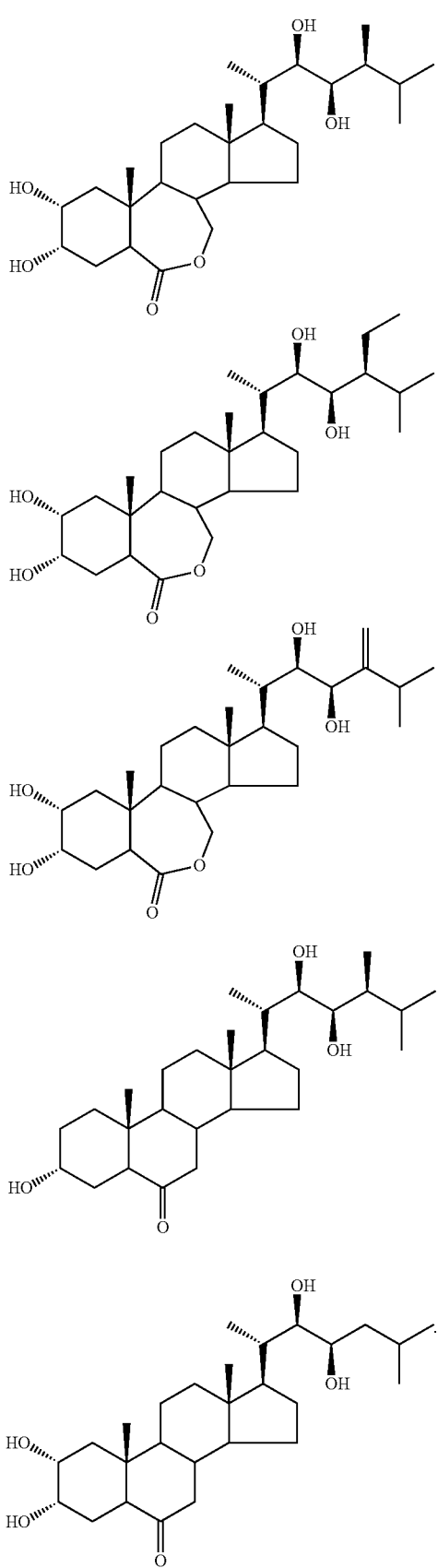

2. The extraction method according to claim 1, wherein in step (1),
the concentration of the aqueous ethanol solution is 85~98° C. (V/V);
the weight-to-volume ratio of the canola pollens:the aqueous ethanol solution is 50~200 g:200-500 mL;
step (1) further comprises the steps of extracting filter residue obtained from the solid-liquid separation by using 80-100° C. (V/V) aqueous ethanol solution, carrying out solid-liquid separation, and retaining filtrate for the combination with the filtrate obtained from step (1);
concentrating is concentrating by drying under reduced pressure, at 65-80° C. and vacuum degree of 0.08-0.09 Mpa; and/or
the volume ratio of the alcohol-soluble liquid extract:the aqueous ethanol solution used in step (2) is 0.5~2:1~3.

3. The extraction method according to claim 1, wherein in step (2),
the concentration of the aqueous ethanol solution is 30~55° C. (V/V);
the volume ratio of the aqueous ethanol solution:the ethyl acetate is 1~3:3~8;
step (2) further comprises the steps of adding ethyl acetate to non-ethyl acetate layer for extraction, and retaining ethyl acetate layer for the combination with the ethyl acetate layer obtained from step (2);
drying is drying under reduced pressure, at 65-80° C. and vacuum degree of 0.08~0.09 Mpa.

4. The extraction method according to claim 1, wherein in step (3),
the packing of the silica gel chromatographic column is 200~300 mesh silica gel;
the volume ratio of methanol:ethyl acetate of the mixture is 3-8:0.5-1.5; and/or
drying is drying under reduced pressure, at 65-80° C. and vacuum degree of 0.08-0.09 Mpa.

5. The extraction method according to claim 1, wherein in step (4),
the volume ratio of acetonitrile:water of the mixture is 60-90:10-40; and/or
the purity of natural brassinolide analogues of formulae BR6, BR1, BR2, BR3, BR4 and/or BR5 is more than 90%.

6. The extraction method according to claim 2, wherein the concentration of the aqueous ethanol solution is 90-97%.

7. The extraction method according to claim 2, wherein the weight-to-volume ration of the canola pollens:the aqueous ethanol solution is 80-150 g:250-450 mL.

8. The extraction method according to claim 2, wherein the volume ratio of the alcohol-soluble liquid extract:the aqueous ethanol solution used in step (2) is 0.8-1.5:1.5-2.5.

9. The extraction method according to claim 3, wherein the concentration of the aqueous ethanol solution is 40-53%.

10. The extraction method according to claim 3, wherein the volume ratio of the aqueous ethanol solution:the ethyl acetate is 1.5-2.5:4-6.

11. The extraction method according to claim 1, wherein the incomplete reaction is a reaction at 37-41° C. for 0.75-1.5 hr.

12. The extraction method according to claim 4, wherein the volume ratio of methanol:ethyl acetate of the mixture is 4-7:0.8-1.3.

13. The extraction method according to claim 5, wherein the volume ratio of acetonitrile:water of the mixture is 70-80:20-30.

* * * * *